US005436381A

United States Patent [19]
Takagawa et al.

[11] Patent Number: 5,436,381
[45] Date of Patent: Jul. 25, 1995

[54] PROCESS FOR PRODUCING A MONOALKENYL AROMATIC HYDROCARBON COMPOUND

[75] Inventors: Makoto Takagawa; Kinji Kato; Norio Fushimi; Ko Kedo, all of Tsukuba, Japan

[73] Assignee: Mitsubishi Gas Chemical Company, Inc., Tokyo, Japan

[21] Appl. No.: 170,495

[22] Filed: Dec. 20, 1993

[30] Foreign Application Priority Data

Feb. 9, 1993 [JP] Japan ................................. 5-021382
Sep. 17, 1993 [JP] Japan ................................. 5-231740

[51] Int. Cl.$^6$ ............................................. C07C 2/72
[52] U.S. Cl. ...................................... 585/452; 585/438; 585/453; 585/463; 585/467
[58] Field of Search ............... 585/452, 453, 463, 467, 585/435, 438

[56] References Cited

U.S. PATENT DOCUMENTS 3,244,758  4/1966  Eberhardt .
3,928,485  12/1975  Nagase et al. .
4,511,748  4/1985  Kudoh et al. ........................ 585/467
4,990,717  2/1991  Sikkenga et al. ................... 585/429

FOREIGN PATENT DOCUMENTS 2103221  4/1972  France .

OTHER PUBLICATIONS

Chemical Abstracts, vol. 119, No. 13, 27 Sep. 1993, p. 836, abstract No. 138842h, Columbus, Ohio, U.S. of JP 5 112 476.

*Primary Examiner*—P. Achutamurthy
*Attorney, Agent, or Firm*—Frishauf, Holtz, Goodman & Woodward

[57] ABSTRACT

There is disclosed a process for producing a monoalkenylbenzene which comprises alkenylating a side chain of an aromatic hydrocarbon compound having at least one hydrogen atom bonded at α-position of the side chain (such as xylene) with a conjugated diene having 4 or 5 carbon atoms (such as butadiene) in the presence of a catalyst produced by calcining the mixture of potassium hydroxide and aluminum hydroxide and then heat treating the calcined product together with metallic sodium in an atmosphere of an inert gas. According to the aforesaid process, an industrially useful monoalkenylbenzene can be produced in high yield at a low cost with enhanced safety.

19 Claims, No Drawings

PROCESS FOR PRODUCING A MONOALKENYL AROMATIC HYDROCARBON COMPOUND

BACKGROUND OF THE INVENTION

1. Field of the Invention

The present invention relates to a process for producing a monoalkenylbenzene. More particularly, it pertains to a process for producing a monoalkenylbenzene by subjecting an aromatic hydrocarbon compound having at least one hydrogen atom bonded at an $\alpha$-position of the side chain to side-chain alkenylation by the use of a conjugated diene having 4 or 5 carbon atoms. A monoalkenylbenzene is useful as the starting intermediate material for various organic compounds typified by high molecular monomers and pharmaceutical preparations. As an example, 5-(o-tolyl)-2-pentene that is produced from oxylene and 1,3-butadiene can be converted into industrially useful 2,6-naphthalene-dicarboxylic acid by ring closure followed by dehydrogenation, isomerization and oxidation.

2. Description of Related Arts

As a process for producing a monoalkenylbenzene by subjecting an aromatic hydrocarbon compound to side-chain alkenylation by the use of a conjugated diene having 4 or 5 carbon atoms, there is known the process in which is employed as a catalyst an alkali metal such as sodium and potassium or an alloy thereof.

For example, German Patent No. 557514 discloses the use of metallic sodium as a catalyst in the above-mentioned process and Eberhardt et al. describes the use of metallic sodium supported on an alkaline earth metal oxide as a catalyst in J. Org. Chem., vol. 30 (1965), pp 82 to 84.

Likewise, there are disclosed the use of metallic potassium in Japanese Patent Publication No. 17973/1975, the use of a potassium/sodium alloy or a mixture of metallic potassium and metallic sodium in Japanese Patent Publication Nos. 17975/1975 and 8930/1976, and the use of metallic potassium supported on an alkali metal oxide or an alkaline earth metal oxide in U.S. Pat. No. 3,244,758 and the aforementioned J. Org. Chem., vol. 30 (1965), pp 82 to 84, each as the catalyst in the above-mentioned process.

There is also disclosed the use of the mixture obtained by heat treating a potassium compound and metallic sodium at 300° C. or a temperature not lower than 350° C. as the catalyst in the above-mentioned process in Japanese Patent Application Laid-Open Nos. 27929/1972 and 31935/1972.

Among the aforestated processes, the process in which is used as a catalyst metallic sodium with or without being supported on an alkaline earth metal oxide is impractical because of insufficiency in both catalytic activity and selectivity of reaction. The process in which is used as a catalyst, metallic potassium, a potassium/sodium alloy or a mixture of metallic potassium and metallic sodium exhibits a high catalytic activity but causes violent reaction of the catalyst with oxygen, moisture and the like. Therefore, an attempt to put the aforesaid process into industrial practice involves various problems on safety due to possible hazards such as fire and explosion.

Likewise, the process in which metallic potassium which is supported on the oxide of an alkali metal or an alkaline earth metal is used as a catalyst involves various problems regarding safety due to the use of the extremely combustible potassium when put into industrial practice.

On the other hand, the process in which is used as a catalyst the mixture obtained by heat treating a potassium compound and metallic sodium at a high temperature is characterized in that the inflammability of metallic potassium and a potassium alloy can be suppressed, but can not be said to be necessarily practical because of insufficient catalytic activity and the necessity for treating the highly inflammable substance at a high temperature.

SUMMARY OF THE INVENTION

It is an object of the present invention to eliminate the various disadvantages of the conventional processes, that is, to provide a process with safety for producing a monoalkenylbenzene in high yield at a low cost in subjecting an aromatic hydrocarbon compound having at least one hydrogen atom bonded at an $\alpha$-position of the side chain to side-chain alkenylation with a conjugated diene having 4 or 5 carbon atoms.

It is another object of the present invention to provide a catalyst for producing a monoalkenylbenzene in high yield at a low cost.

Other objects of the present invention will be obvious from the description of this text hereinafter disclosed.

Under the above-mentioned circumstances, intensive research and investigation were made by the present inventors in order to attain the above-described objects. As a result, it has been found by the present inventors that a monoalkenylbenzene can be produced with assured safety in high yield at a low cost by the use of a solid base-catalyst obtained by adding metallic sodium to the compound produced by calcining the mixture of potassium hydroxide and aluminum hydroxide and heat treating the resultant mixture under an atmosphere of an inert gas at the melting point of sodium or higher. The present invention has been accomplished on the basis of the above-mentioned finding.

The catalyst which is prepared according to the process of the present invention has remarkably high activity in the side-chain alkenylation reaction of an aromatic hydrocarbon compound with a conjugated diene, and sufficient activity of the catalyst is obtained even if the catalyst is prepared by heat treatment at a relatively low temperature provided that the temperature is not lower than the melting point of metallic sodium, that is, 97.8° C. In addition, even a relatively small amount of the catalyst enables the production of a monoalkenylbenzene in high yield and in high selectivity with facility in handling the catalyst.

By virtue of the extremely high activity of the catalyst according to the present invention, the alkenylation reaction proceeds satisfactorily even under exceptionally mild reaction conditions including atmospheric pressure and a temperature of 100 to 200° C.

Specifically, the present invention provides a process for producing a monoalkenylbenzene by alkenylating a side chain of an aromatic hydrocarbon compound having at least one hydrogen atom bonded to an $\alpha$-position of the side chain by using a conjugated diene having 4 to 5 carbon atoms which process comprises effecting said alkenylation by the use of a catalyst composition produced by a method wherein the compound obtained by calcining the mixture of potassium hydroxide and aluminum hydroxide at 400 to 700° C. is heat treated along with metallic sodium at 100 to 300° C. in an atmosphere of an inert gas.

DESCRIPTION OF PREFERRED EMBODIMENT

Examples of the specific aromatic hydrocarbon compound having at least one hydrogen atom bonded at an α-position of the side chain to be employed as the starting raw material in the present invention include monocyclic aromatic hydrocarbons such as monoalkylbenzenes enumerated by toluene; ethylbenzene; n-propylbenzene; isopropylbenzene; n-butylbenzene; secbutylbenzene; and isobutylbenzene, dialkylbenzenes enumerated by o-, m- and p-xylenes; o-, m- and p-ethyltoluenes; and o-, m- and p-diethylbenzenes, trialkylbenzenes enumerated by mesitylene; and pseudocumene and polyalkylbenzenes enumerated by 1,2,3,5-tetramethylbenzene; 1,2,4,5-tetramethylbenzene; pentamethylbenzene; and hexamethylbenzene, and polycycic aromatic hydrocarbons such as 1- and 2-methylnaphthalenes, dimethylnaphthalenes, alkyl tetrahydronaphthalenes and alkyl indanes.

As the conjugated dienes having 4 or 5 carbon atoms as another starting raw material, there are preferably used 1,3-butadiene; 1,3-pentadiene; and isoprene.

The aluminum hydroxide to be used in preparing the catalyst according to the present invention includes gibbsite, bayerite, norstrandite, boehmite, boehmite gel, diaspore or the like expressed in terms of mineral nomenclature; amorphous alumina gel; and so called aluminum hydroxide available in the market.

The potassium hydroxide to be compounded with the aluminum hydroxide may contain the hydroxide of an alkali metal other than potassium such as sodium hydroxide and lithium hydroxide and the carbonate of an alkali metal up to the amount equimolar with potassium.

As mentioned hereinbefore, the catalyst to be used in the process of the present invention is prepared by mixing the above-mentioned aluminum hydroxide and potassium hydroxide, calcining the resultant mixture and heat treating the calcined product along with metallic sodium, which may contain an alkali metal other than sodium to the extent equimolar therewith.

In the case of mixing the potassium hydroxide and aluminum hydroxide either a wet system or a dry system is acceptable provided that both the hydroxides are sufficiently mixed with and dispersed in each other. However, a wet system is preferable for the purpose of homogeneous dispersion.

As the method of preparing the mixture by a wet system there is available a method in which aluminum hydroxide is added to the aqueous solution of potassium hydroxide to form a mixed solution, which is agitated, mixed and then dried. There is also available, in the case of a dry system, a method in which both the hydroxides are mixed with heating at a temperature higher than the melting point of potassium hydroxide, that is, at 360° C. or higher. The mixture thus obtained contains various precursors of potassium aluminates formed during the mixing, whose homogeneous dispersion in the mixture is of importance in preparing a highly active catalyst.

The mixture obtained by any of the above-mentioned methods is calcined and subsequently mixed with metallic sodium.

The calcination temperature is in the range of 400 to 700° C., preferably 500 to 650° C. The aforesaid temperature range is significant for producing the highly active catalyst and believed to be responsible for the formation of various potassium aluminares by calcination, which exhibit high catalytic-activity. It is therefore, necessary that the calcination temperature be high enough to form the various aluminates, that is, 400° C. or higher, preferably 500° C. or higher. Conversely, an unnecessarily high calcination temperature results in failure to sufficiently disperse metallic sodium and produce highly active catalyst in the case of mixing the metallic sodium and the calcined product to finally constitute the catalyst composition. Accordingly, the calcination temperature should be 700° C. or lower, preferably 650° C. or lower.

The mixing ratio by atomic ratio of the potassium hydroxide to the aluminum hydroxide is 0.3 to 3, preferably 0.5 to 2 in terms of the ratio of potassium atoms in the potassium hydroxide to aluminum atoms in the aluminum hydroxide (K/Al atomic ratio). The calcined product produced in the range of the above-mentioned mixing ratio is composed of various alminates that are effective as the carrier which favorably disperses the metallic sodium. The mixing ratio should be determined from the viewpoint of effectively producing the aluminate taking into consideration the relation with the calcination temperature.

An amount of potassium hydroxide less than the lower limit of the aforesaid mixing ratio leads to such disadvantages that side reaction such as the isomerization of the alkenylbenzene to be produced is likely to occur, the deterioration of catalytic activity is accelerated, and an unreasonably large amount of the catalyst is needed to maintain the high activity of the catalyst, whereby the post-treatment after the reaction is complicated, whereas an amount thereof more than the above higher limit unfavorably makes it hardly possible to manifest the effect due to the use of the aluminum hydroxide and prepare the catalyst which is highly active and easy to handle.

The compounds that are produced by mixing and calcining the aluminum hydroxide and potassium hydroxide according to the above-mentioned conditions are composed of various aluminates such as $K_3AlO_3$, $K_2Al_2O_4$, $KAl_3O_5$ and $KAl_5O_8$. The proportion of each aluminate present in the calcined product varies depending on the mixing ratio of the aluminum hydroxide to the potassium hydroxide, method of preparation and the like. At any rate, the existence of the above-mentioned aluminates enables the production of highly active catalyst.

The preparation of the catalyst by mixing the product prepared from the aluminum hydroxide and the potassium hydroxide with metallic sodium is carried out by mixing with heating the mixture in an atmosphere of an inert gas at a temperature not lower than the melting point of metallic sodium. By the term "inert gas" as mentioned herein is meant a gas that is substantially non-reactive with the catalyst to be prepared under the preparation conditions for the catalyst, which inert gas is exemplified by nitrogen, helium and argon.

Heat-treatment in the preparation of the catalyst to be used in the present invention is carried out at a temperature in the range of the melting point of metallic sodium to 500° C., desirably 100 to 300° C. The heating treatment time is usually in the range of 5 to 300 minutes.

Metallic sodium, when incorporated with potassium or the like, is brought into the form of liquid at a temperature lower than the melting-point of sodium. In the above case, the catalyst can be prepared without any difficulty provided that the potassium-containing sodium is maintained at a temperature not lower than the temperature at which it is brought into the form of liquid.

In the case where the metallic sodium is not melted, the catalyst preparation results in difficulty in homogeneously dispersing metallic sodium in the product prepared from the hydroxides of aluminum and potassium and in bringing metallic sodium into effective contact with the above product, thereby requring a long preparation time and rendering itself impractical. On the other hand, although the catalyst can be prepared at a temperature exceeding 500° C., it can not be said that handling of an inflammable substance at a high temperature is favorable in industrial practice.

The amount of the metallic sodium to be used in the preparation of the catalyst according to the present invention is determined so that the atomic ratio of sodium atoms in metallic sodium to potassium atoms in the potassium hydroxide is 0.01 to 5, preferably 0.1 to 3. An amount of metallic sodium less than the above range unfavorably results in failure to sufficiently exert the effect due to the use of metallic sodium and the potassium hydroxide, thereby necessitating an unreasonably large amount of the catalyst to assure the required catalytic activity. On the other hand, an amount thereof more than the above range leads to failure to sufficiently disperse the metallic sodium in the product from the hydroxides of aluminum and potassium, thus causing unfavorable result from the viewpoint of safety and catalyst handling.

In employing the catalyst according to the present invention thus obtained in the alkenylation reaction, various reaction systems are available and exemplified by a batchwise or a semi-batchwise system in which the starting raw material is fed batchwise or semi-batchwise into the reactor which has previously been fed with the catalyst; a complete mixing system in which the catalyst and starting raw material are continuously fed into a reactor; and a flow system through a fixed bed in which the starting raw material is allowed to flow through the reactor which has previously been packed with the catalyst. The reaction system should be suitably selected in accordance with the type of the objective reaction product. In general, the selectivity to the objective monoalkenylbenzene can be enhanced by the system wherein an aromatic hydrocarbon as one of the starting raw materials is allowed to be present in excess against a conjugated diene. For the purpose of enhancing the selectivity, a semi-batchwise system is preferable in which a conjugated diene is continuously fed into the reaction system. In the case of a continuous reaction by a complete mixing system or a flow system through a fixed bed, it is preferable for enhancing the selectivity to adopt the reaction system capable of lowering the concentration of a conjugated diene in the reactor such as the system in which a conjugated diene is fed into each stage of a multistage reactor to be adopted.

The reaction between the aromatic hydrocarbon and the conjugated diene in the process according to the present invention is carried out under the conditions in which the aromatic hydrocarbon as the starting raw material and the objective product are substantially in the form of liquid.

The reaction temperature in the process according to the present invention is in the range of 50 to 300° C., preferably 100 to 200° C. A temperature lower than the above lower limit can cause the reaction to take place, but results in failure to attain a sufficient reaction rate; and besides tends to lower the selectivity, while that higher than the above higher limit unfavorably leads to an increased amount of byproduct such as tar components. The reaction is more preferably carried out at the reflux temperature or lower when it is lower than 200° C. from the viewpoint of keeping the reaction conditions in which the starting raw material and the objective product are substantially in the form of liquid.

The reaction pressure is not specifically limited insofar as the aromatic hydrocarbon as the starting raw material and the objective product are present substantially in the form of liquid. It is in the range of 0.05 to 5 absolute atmospheric pressure ($0.05 \times 10^5$ to $5.07 \times 10^5$ Pa), preferably 0.1 to 2 absolute atmospheric pressure ($0.10 \times 10^5$ to $2.03 \times 10^5$ Pa).

In the process according to the present invention, the molar ratio of the conjugated diene having 4 to 5 carbon atoms as another starting raw material to the aromatic hydrocarbon as a starting raw material is generally 0.01 to one (1), preferably 0.03 to 0.5. A molar ratio thereof higher than the above higher limit unfavorably causes an increase in the formation of the compound namely, the monoalkenylbenzene thus produced is further reacted with the excess diene to allow the addition of at least two molecules of the diene to one molecule of the aromatic hydrocarbon and the likelihood of diene polymerization, whereby the selectivity to the objective compound is undesirably worsened.

The amount of the catalyst to be used in the process according to the present invention is 0.01% or more, preferably 0.05% or more by weight based on the amount of the aromatic hydrocarbon as a starting raw material.

As described hereinbefore, the reaction system is selected from a batchwise system, a semi-batchwise system, a complete mixed flow system and the like in putting the process of the invention into practice. There is usually adopted 0.1 to 10 hours as the reaction time in a batchwise and a semi-batchwise system and as the retention time in complete mixing system. In the case of a flow system through a fixed bed, liquid hourly space velocity (LHSV) for the aromatic hydrocarbon in the range of 0.1 to 10 $h^{-1}$ is usually selected.

In the case of carrying out the reaction with a suspended catalyst, the separation of the reaction liquid from the catalyst after the reaction can easily be performed by any of the conventional methods including sedimentation, centrifugal separation and filtration. The separated catalyst may be circulated through the reaction system or subjected to the necessary step such as removing organic substances attached thereto by combustion with air and cleaning with water, followed by circulation through a catalyst preparation step.

The process according to the present invention is capable of producing a monoalkenylbenzene having industrial availability from an aromatic hydrocarbon compound and a conjugated diene in high reaction performance at a low cost with enhanced safety, thus rendering itself extremely significant from the industrial viewpoint.

In the following, the present invention will be described in more detail with reference to the examples, but shall not be limited thereto.

EXAMPLE 1

To an aqueous solution of 61.0 g of potassium hydroxide (KOH) was added 85.0 g of aluminum hydroxide [Al(OH)] powder (produced by Nippon Light Metal Co., Ltd.) under stirring for mixing at room temperature for one hour. The mixture was dried overnight at 115° C. and then calcined in air at 550° C. Thereafter, 5 g of the calcined product was stirred at 150° C. in a nitrogen atmosphere and incorporated with 0.80 g of metallic sodium, followed by stirring for 30 min. at the resulting temperature (150° C.).

The powdery catalyst thus obtained was incorporated, in a stream of nitrogen, with 1000 g of o-xylene that had been dehydrated with molecular sieve, and subsequently the resultant mixture was heated to 140° C. Then 50 g of 1,3-butadiene was introduced into the reaction system over a period of one hour with stirring to carry out the side-chain alkenylation reaction. After cooling the reaction system, the catalyst was deactivated by adding isopropyl alcohol thereto and then the reaction liquid was sampled for analysis by gas chromatography. The reaction results are given in Table 1.

EXAMPLES 2 TO 5

The procedure in Example 1 was repeated to prepare the catalysts and carry out the reaction by the use thereof except for alteration in the mixing ratio of KOH to $Al(OH)_3$, calcination temperature, amount of calcined product, amount of metallic sodium, treatment temperature and treatment time as described in Table 1. The reaction results are given in Table 1. The treatment temperature and the treatment time are the temperature and the time, respectively in mixing the metallic sodium with the product prepared from $Al(OH)_3$ and KOH.

EXAMPLE 6

The procedure in Example 1 was repeated to prepare the catalyst and carry out the reaction except that a mixture of KOH and NaOH was employed in place of KOH alone. The reaction results are given in Table 1.

EXAMPLE 7

The procedure in Example 1 was repeated to prepare the catalyst and carry out the reaction except that 1,3-butadiene was fed in an amount of 70 g instead of 50 g. The reaction results are given in Table 1.

COMPARATIVE EXAMPLE 1

The procedure in Example 1 was repeated to prepare the catalyst and carry out the reaction except that 43.6 g of sodium hydroxide (NaOH) was used in place of 61.0 g of potassium hydroxide (KOH). The reaction results are given in Table 1.

COMPARATIVE EXAMPLES 2 AND 3

The procedure in Example 1 was repeated to prepare the catalyst and carry out the reaction except that the calcination temperature of the mixture of KOH and $Al(OH)_3$ was altered. The reaction results are given in Table 1.

COMPARATIVE EXAMPLE 4

5 g of potassium carbonate powder that had been calcined at 550° C. was heated to 350° C. in nitrogen, incorporated with 1.2 g of metallic sodium with stirring and further heated at the resulting temperature for 120 minutes to prepare the catalyst. After allowing the catalyst to cool to the reaction temperature, the reaction was performed in the same manner as in Example 1. The reaction results are given in Table 1.

COMPARATIVE EXAMPLE 5

The procedure in Example 1 was repeated to carry out the reaction except that 5.0 g of metallic sodium was used as the catalyst. The reaction results are given in Table 1.

COMPARATIVE EXAMPLE 6

The procedure in Example 1 was repeated to carry out the reaction except that 1.0 g of metallic potassium was used as the catalyst. The reaction results are given in Table 1.

COMPARATIVE EXAMPLE 7

The procedure in Example 1 was repeated to prepare the catalyst and carry out the reaction except that potassium aluminate trihydrate (produced by Kanto Chemical Co., Ltd.) was calcined at 550° C. in the air and 5 g of the calcined product was employed. The reaction results are given in Table 1.

TABLE 1

| | Type of alkali-metal hydroxide (atomic ratio based on Al)[*1] | Calcination temperature (°C.) | Usage of [*2] mixture (g) | Amount of metalic Na (g) (Na/K atomic ratio) | Treatment[*3] temperature (°C.) | Treatment[*4] time (min.) | OTP[*5] yield (%) |
|---|---|---|---|---|---|---|---|
| Example 1 | KOH (1.0) | 550 | 5.0 | 0.80 (0.7) | 150 | 30 | 89.8 |
| Example 2 | KOH (0.7) | 600 | 5.0 | 0.70 (0.75) | 130 | 60 | 90.1 |
| Example 3 | KOH (1.0) | 650 | 5.0 | 1.00 (0.85) | 150 | 60 | 88.6 |
| Example 4 | KOH (1.5) | 550 | 5.0 | 0.70 (0.5) | 180 | 30 | 88.7 |
| Example 5 | KOH (0.6) | 600 | 3.0 | 1.0 (1.9) | 150 | 60 | 89.2 |
| Example 6 | KOH (0.8) NaOH (0.6) | 550 | 10.0 | 0.60 (0.7) | 150 | 20 | 89.0 |
| Example 7 | KOH (1.0) | 550 | 5.0 | 0.80 (0.7) | 150 | 30 | 82.7 |
| Comparative Example 1 | NaOH (1.0) | 550 | 5.0 | 1.0 (0.7)[*6] | 150 | 60 | 8.2 |
| Comparative Example 2 | KOH (1.0) | 350 | 5.0 | 0.80 (0.7) | 150 | 30 | 52.8 |
| Comparative Example 3 | KOH (1.0) | 750 | 5.0 | 0.80 (0.7) | 150 | 30 | 66.3 |
| Comparative Example 4 | $K_2CO_2$ | 550 | 5.0 | 1.2 (0.7) | 350 | 120 | 78.3 |
| Comparative Example 5 | — | — | — | 5.0 | — | — | 5.3 |
| Comparative Example 6 | — | — | — | K 1.0 | — | — | 83.2 |
| Comparative | $K_2Al_2O_4$ | 550 | 5.0 | 0.80 (0.7) | 150 | 30 | 84.9 |

TABLE 1-continued

| Type of alkali-metal hydroxide (atomic ratio based on Al)*1 | Calcination temperature (°C.) | Usage of*2 mixture (g) | Amount of metalic Na (g) (Na/K atomic ratio) | Treatment*3 temperature (°C.) | Treatment*4 time (min.) | OTP*5 yield (%) |
| --- | --- | --- | --- | --- | --- | --- |
| Example 7 | | | | | | |

*1 Atomic ratio of alkali metal in alkali-metal hydroxide to Al
*2 Calcined product of mixture of alumina hydroxide d alkali-metal hydroxide
*3 Temperature in mixing metallic sodium with the product prepared from aluminum hydroxide and potassium hydroxide.
*4 Period of time in mixing metallic sodium with the product prepared form aluminum, hydroxide and potassium hydroxide.
*5 OTP: 5-(O-tolyl)-2-pentene
*6 Atomic ratio of metallic sodium to sodium in alkali-metal hydroxide

EXAMPLE 8

The powdery catalyst that had been prepared in the same manner as in Example 1 was incorporated, in a stream of nitrogen, with 1000 g of o-xylene that had been dehydrated with molecular sieve, and subsequently the resultant mixture was heated to 130° C. Subsequently 50 g of 1,3-butadiene was introduced into the reaction system with vigorous stirring for one hour to carry out the reaction. The reaction product was cooled and allowed to stand to sediment the catalyst powder. The resultant reaction liquid was taken out in almost the entire amount by means of decantation and sampled for analysis by gas chromatography. The reaction results are given in Table 2.

EXAMPLE 9

The catalyst slurry that had been used for the reaction and left after the recovery of almost the entire amount of the reaction liquid in Example 8 was incorporated, in a stream of nitrogen, with 1000 g of o-xylene, and subsequently the mixture was heated to 130° C. Subsequently 50 g of 1,3-butadiene was introduced into the reaction system over a period of one hour with vigorous stirring to proceed with reaction. The procedure was repeated 5 times to proceed with the reaction in the same manner by the use of the catalyst left each time after the reaction liquid was taken out in almost the entire amount by means of decantation, and thereafter, the catalyst was deactivated by adding isopropyl alcohol thereto and then the reaction liquid was sampled for analysis by gas chromatography. The reaction results are given in Table 2.

EXAMPLE 10

The powdery catalyst that had been prepared in the same manner as in Example 1 was incorporated, in a stream of nitrogen, with 1000 g of m-xylene that had been dehydrated with molecular sieve, and subsequently the resultant mixture was heated to 135° C. Subsequently 50 g of 1,3-butadiene was introduced into the reaction system over a period of one hour with vigorous stirring to carry out the reaction. After cooling the reaction system, the catalyst was deactivated by adding isopropyl alcohol thereto and then the reaction liquid was sampled for analysis by gas chromatography. The reaction results are given in Table 2.

EXAMPLES 11 AND 12

The procedure in Example 10 was repeated to carry out the reaction except that p-xylene or ethylbenzene was employed in place of m-xylene. The reaction results are given in Table 2.

TABLE 2

| | Aromatic hydrocarbon as starting material | Objective product | Yield (%) |
| --- | --- | --- | --- |
| Example 8 | o-xylene | 5-(o-tolyl)-2-pentene | 89.3 |
| Example 9 | o-xylene | 5-(o-tolyl)-2-pentene | 88.7 |
| Example 10 | m-xylene | 5-(m-tolyl)-2-pentene | 86.2 |
| Example 11 | p-xylene | 5-(p-tolyl)-2-pentene | 85.0 |
| Example 12 | ethylbenzene | 5-phenyl-2-hexene | 83.3 |

What is claimed is:

1. A process for producing a monoalkenyl aromatic hydrocarbon compound comprising alkenylating a side chain of an aromatic hydrocarbon compound having at least one hydrogen atom bonded to an α-position of the side chain with a conjugated diene having 4 to 5 carbon atoms at a pressure of $0.05 \times 10^5$ to $5.07 \times 10^5$ Pa in the presence of a catalyst composition produced by calcining a mixture of potassium hydroxide and aluminum hydroxide at a temperature of 500 to 650° C. to form a calcined mixture and heat treating the calcined mixture with metallic sodium at a temperature of 100 to 300° C. in an inert gas atmosphere.

2. The process according to claim 1 wherein the aluminum hydroxide is at least one member selected from the group consisting of gibbsite, bayerire, norstrandite, boehmite, boehmite gel, diaspore and amorphous alumina gel.

3. The process according to claim 1 wherein the mixture to be calcined further contains at least one hydroxide of an alkali metal selected from the group consisting of sodium hydroxide and lithium hydroxide up, to an amount equimolar with the potassium.

4. The process according to claim 1 wherein the metallic sodium further contains potassium up to an amount equimolar with the sodium.

5. The process according to claim 1 wherein the mixture of potassium hydroxide and aluminum hydroxide is prepared by a method in which aluminum hydroxide is added to an aqueous solution of potassium hydroxide and the resultant mixture is agitated and then dried.

6. The process according to claim 1 wherein a mixing ratio of the potassium hydroxide to the aluminum hydroxide is 0.3 to 3 expressed in terms of the ratio of potassium atoms in the potassium hydroxide to aluminum atoms in the aluminum hydroxide.

7. The process according to claim 1 wherein the heat treating is effected for 5 to 300 minutes.

8. The process according to claim 1 wherein the metallic sodium is employed in the heat treating in a ratio of 0.01 to 5 expressed in terms of an atomic ratio of sodium to potassium in the potassium hydroxide.

9. The process according to claim 1 wherein the alkenylation is carried out at a reaction temperature of 100° C. to the reflux temperature under a reaction pressure of at most $2.03 \times 10^5$ Pa.

10. The process according to claim 1 wherein the aromatic hydrocarbon compound is selected from the group consisting of toluene, ethylbenzene, n-propylbenzene, isopropylbenzene, n-butylbenzene, sec-butylbenzene, isobutylbenzene, o-xylene, m-xylene, p-xylene, o-ethyltoluene, m-ethyltoluene, p-ethyltoluene, o-diethylbenzene, m-diethylbenzene, p-diethylbenzene, mesitylene, pseudocumene, 1,2,3,5-tetramethylbenzene, 1,2,4,5-tetramethylbenzene, pentamethylbenzene, hexamethylbenzene, 1-methylnaphthalene, 2-methylnaphthalene, dimethylnaphthalene, alkyl tetrahydronaphthalene and alkyl indane.

11. The process according to claim 10 wherein the conjugated diene is selected from the group consisting of 1,3-butadiene; 1,3-pentadiene; and isoprene.

12. The process according to claim 11 wherein a mixing ratio of the potassium hydroxide to the aluminum hydroxide is 0.05 to 2 expressed in terms of a ratio of potassium atoms in the potassium hydroxide to aluminum atoms in the aluminum hydroxide.

13. The process according to claim 12 wherein the metallic sodium is employed in the heat treating in a ratio of 0.1 to 3 expressed in terms of an atomic ratio of sodium to potassium in the potassium hydroxide.

14. The process according to claim 13 wherein the alkenylation is carried out at a reaction temperature of 100° C. to 200° C. under a reaction pressure of $0.10 \times 10^5$ to $2.03 \times 10^5$ Pa.

15. The process according to claim 14 wherein a molar ratio of the conjugated diene to the monoalkenylbenzene is 0.01 to 1.

16. The process according to claim 14 wherein a molar ratio of the conjugated diene to the monoalkenylbenzene is 0.03 to 0.5.

17. The process according to claim 16 wherein the catalyst is in an amount of 0.01 weight % or more based on the amount of the monoalkenylbenzene.

18. The process according to claim 16 wherein the catalyst is in an amount of 0.05 weight % or more based on the amount of the monoalkenylbenzene.

19. The process according to claim 18 wherein the alkenylation is carried out for 0.1 to 10 hours at a liquid hourly space velocity of 0.1 to 10 hours$^{-1}$.